United States Patent
Naylor et al.

[11] Patent Number: 5,491,299
[45] Date of Patent: Feb. 13, 1996

[54] FLEXIBLE MULTI-PARAMETER CABLE

[75] Inventors: Thomas K. Naylor, Belmont; Helen C. Crouse, Waltham, both of Mass.; Edwin Muz, Reutlingen, Germany

[73] Assignee: Siemens Medical Systems, Inc., Iselin, N.J.

[21] Appl. No.: 253,518

[22] Filed: Jun. 3, 1994

[51] Int. Cl.⁶ .................................................. H01B 7/34
[52] U.S. Cl. .................. 174/36; 174/105 R; 174/113 R; 174/115
[58] Field of Search .................. 174/36, 113 R, 174/115, 105 R

[56] References Cited

U.S. PATENT DOCUMENTS

| Re. 27,206 | 10/1971 | Gabriel | 325/308 |
|---|---|---|---|
| 4,110,554 | 8/1978 | Moore et al. | 174/101.5 |
| 4,158,478 | 6/1979 | D'Auria et al. | |
| 4,294,504 | 10/1981 | Siewerdt | |
| 4,461,923 | 7/1984 | Bogese, II | 174/36 |
| 4,538,022 | 8/1985 | Barnicol-Ottler et al. | 174/113 R |
| 4,552,432 | 11/1985 | Anderson et al. | |
| 4,719,319 | 1/1988 | Tighe, Jr. | 174/103 |
| 4,920,234 | 4/1990 | Lemke | 174/36 |
| 5,149,915 | 9/1992 | Brunker et al. | 174/36 |
| 5,150,442 | 9/1992 | Desmons | 385/101 |

FOREIGN PATENT DOCUMENTS

| 0466272 | 7/1991 | European Pat. Off. . |
|---|---|---|
| 0553372 | 8/1993 | European Pat. Off. . |
| 524992 | 8/1972 | Switzerland . |

*Primary Examiner*—Morris H. Nimmo
*Attorney, Agent, or Firm*—Lawrence C. Edelman

[57] ABSTRACT

A flexible multi-parameter conductor cable having coaxially symmetric elongated zones for signal carrying conductor placement therein, comprising an electrically conductive inner shield defining an electrically shielded inner longitudinal zone symmetrically disposed along and defining a center of said cable for containing at least one of a first type of signal carrying conductor, and an electrically conductive outer shield spaced a given distance symmetrically around said inner shield so as to define an electrically shielded outer longitudinal zone symmetrically disposed about said inner longitudinal zone for containing a plurality of at least a second type of signal carrying insulated conductor arranged in a single layer adjacent one another in said second longitudinal zone, said second type of conductor having an electrically conductive outer jacket in electrical contact with at least said outer shield.

15 Claims, 3 Drawing Sheets

FLEXIBLE MULTI-PARAMETER CABLE

BACKGROUND OF THE INVENTION

1. Field of the Invention

The present invention relates to a flexible multi-parameter cable having a plurality of different types of conductors for conducting signals relating to a plurality of different types of sensed parameters, and more particularly to a multi-conductor patient monitoring cable for conducting signals such as electrocardiogram, respiration, temperature and pulse oximetry signals, relating to a plurality of different types of sensed physiological conditions of a patient.

2. Description of the Prior Art

In hospitals and other health care environments, it is often necessary to continually collect and analyze a variety of different types of medical data from a patient. These data may include electrocardiogram (EKG) signals, body temperature, blood pressure, respiration, blood oxygen saturation, and other monitored physiological parameters.

Medical monitoring systems have typically fallen into one of two general categories: multi-parameter monitoring systems which collect, process and display all of the desired data; and small portable systems which monitor one or two of the various patient physiological parameters. Multi-parameter monitoring is typically provided at a higher care facility, such as an intensive care unit or hospital operating room, and generally results in a plurality of cables which extend between the patient and the monitor. For example, there may be anywhere from three to five cables for EKG, two for cardiac output, three for temperature, six for non-invasive pulse oximetry, etc. This array of cables interferes with the movement of personnel around the patient and furthermore presents an undesirable obstacle when the patient must be quickly transferred from one position to another, such as from his room bed to an operating room or an intensive care unit.

FIG. 1a illustrates a typical prior art arrangement wherein a patient 2 has a plurality of sensor leads, such as EKG leads 4, non-invasive pulse oximetry leads 6, temperature leads 8 and an air hose 10 for non-invasive blood pressure measurement, connected between the corresponding sensor apparatus on patient 2 and a respective one of monitor cables 12, 14, 16 and 18. Each of monitor cables 12–18 typically include a connector at one end which is received by a patient monitor 20 and a connector at its other end which receives the patient connected sensor leads 4–10.

One prior art attempt to provide management of the plurality of different types of leads and cables in a patient monitoring system is shown in, for example, Swiss Patent 524,992 and EPO 0 466 272. In these prior publications, it is indicated that a single junction box can receive each of the patient connected leads coupled to the individual patient sensors, and provide a common output cable from the junction box which is then connected to the patient monitor. Although the construction of the single output cable is not disclosed in these patents, it is expected that it merely comprises a bundling of the individual patient leads into a single jacketed structure, such as shown in FIG. 1b. Bundling is a conventional technique for cable management, as evidenced by U.S. Pat. No. 27,206. Although use of a single output cable improves cable management, there are serious electrical and mechanical problems associated with such a system. For example, the EKG sensors, being connected to the skin of the patient, are susceptible to picking-up very high voltage and/or high frequency signals when electrosurgery is being performed on the patient, or in the event that defibrillation becomes necessary. Under these circumstances the high voltage signals picked-up by the EKG leads may cause electromagnetic interference (EMI) which may be impressed upon the conductors carrying the other sensed patient signals, and thereby distort or otherwise corrupt these other signals. Furthermore, it is noted that when performing, for example, pulse oximetry sensing, it is required to provide relatively high current pulse signals to the oximetry sensor apparatus and a very low level and noise sensitive receive signal is required to be sensed and provided back to the monitor. Thus, when EKG cables are bundled in close proximity with pulse oximetry cables, the high level pulse currents on the pulse oximetry conductors can create electrical disturbances on the EKG signal conductors, and conversely, the high voltage signals on the EKG conductors can corrupt the data in the very sensitive pulse oximetry receive conductors. Still, furthermore, the EKG conductors can crosstalk among themselves, due to their being bundled together, and thereby degrade the common mode rejection of one pair of EKG conductors with respect to another pair. Even furthermore, the pick-up of high voltage defibrillation pulses by the EKG conductors can cause a breakdown of the voltage isolation between the closely spaced pins of the cable connector at the cable/monitor interface. Due to these electrical problems, a single cable which merely comprises a collection of the individual patient parameter cables bundled so as to be included in a single sheath, may be inadequate. Additionally, from a mechanical point of view, a cable as shown in FIG. 1b would be relatively heavy, thick, inflexible and bulky due to the plurality of individual shields and outer jackets included with each patient cable, as well as the requirement for a plurality of interstitial fillers which are added for improving the shape of the cable, but which unfortunately adds to its weight and inflexibility. Still further, due to the separated and non-symmetrically spaced arrangement of the cable bundles, each bundle, and each conductor in each bundle, must be constructed so as to have a maximum resistance to flexing failure. This necessarily increases the cost and complexity of the multi-parameter cable.

Another solution to the multi-parameter cable problem would be to provide active electrical signal processing inside of the junction box which would multiplex the multiple patient parameter signals onto a single output conductor or coaxial cable which is then received and demultiplexed by the monitor. Although this appears to be a satisfactory solution, it causes the junction box to become a much more expensive device, as well as undesirably increasing its size, introducing power requirements and decreasing its reliability. Additionally, since the junction box is positioned at the free end of the monitor cable, it is subject to being dropped on the floor, etc., when disconnected from the patient and therefore size, weight, flexibility and durability (as well as cost) are very important considerations.

Consequently, it is desirable to provide a multi-conductor cable which will provide continuity of the electrical signal handling properties of the leads connected to a plurality of different parameter sensors, when these leads are combined in a single multi-conductor cable, while at the same time prevent cross coupling of the signals. At the same time, it is desirable that this cable be flexible, light, of a small diameter, cost effective and relatively easy to construct.

SUMMARY OF THE INVENTION

In accordance with the principles of the present invention, a multi-parameter cable is provided for use to connect insulated conductors from a plurality of different types of sensors to a monitoring device, comprising a first tubular sheath to define a central zone of the multi-parameter cable for carrying signal to and/or from a first type of the sensors, and an electrically conductive second tubular sheath spaced a given distance symmetrically about the central zone to define an outer zone for containing a plurality of insulated conductors coupled to a second type of said sensors. The insulated conductors coupled to the second type of sensor are arranged in a single layer adjacent one another in the outer zone and include an electrically conductive outer jacket which is in electrical contact with the second tubular sheath.

In accordance with a further aspect of the invention, a plurality of insulated conductors coupled to a third type of sensor are also arranged in a single layer adjacent one another in the outer zone, with the insulated conductors coupled to said third type of sensor having an insulating outer jacket and the outer jackets of all of the insulated conductors coupled to both of the second and third types of sensors which are in said outer zone have an outer diameter which is substantially the same. Still further, the outer diameter is equal to the given distance between the first and second tubular sheaths.

In accordance with a still further aspect of the invention, the first sheath is also electrically conductive and thereby divides the multi-parameter cable into three electrically isolated zones, namely the central zone, and two portions in the outer zone, one comprising that portion of the outer zone wherein the conductors of the second type are arranged adjacent one another and the other zone being the remainder of the outer zone. This arrangement is particularly advantageous in that only two conductive shields, namely the first and second conductive sheaths, are required, thereby reducing the shielding requirement for each of the individual conductors from that which would normally be required when signal conductors are closely bundled in a common cable. The reduced shielding requirement for the individual conductors leads to a lower cost, lower weight, 772 smaller and more flexible multi-parameter cable.

In accordance with an even further aspect of the invention, the signal conductors which are contained in the central zone are twisted so that the lay or twist rate of the conductors in the central zone are different, and preferably twice, than the lay of the conductors in the outer zone. With this arrangement the electromagnetic coupling of the signals in the central zone to the conductors in the outer zone of the cable is minimized.

In accordance with a still further aspect of the invention, the conductors and shields of the outer zone are constructed of a material having a greater resistance to flexing failure than the conductors and shields of the central zone, thereby allowing lower cost materials to be used for constructing the central zone of the cable.

Other features and advantages of the invention will be suggested by the following description, with reference to the appended figures of which:

DETAILED DESCRIPTION OF THE INVENTION

Figure 2:
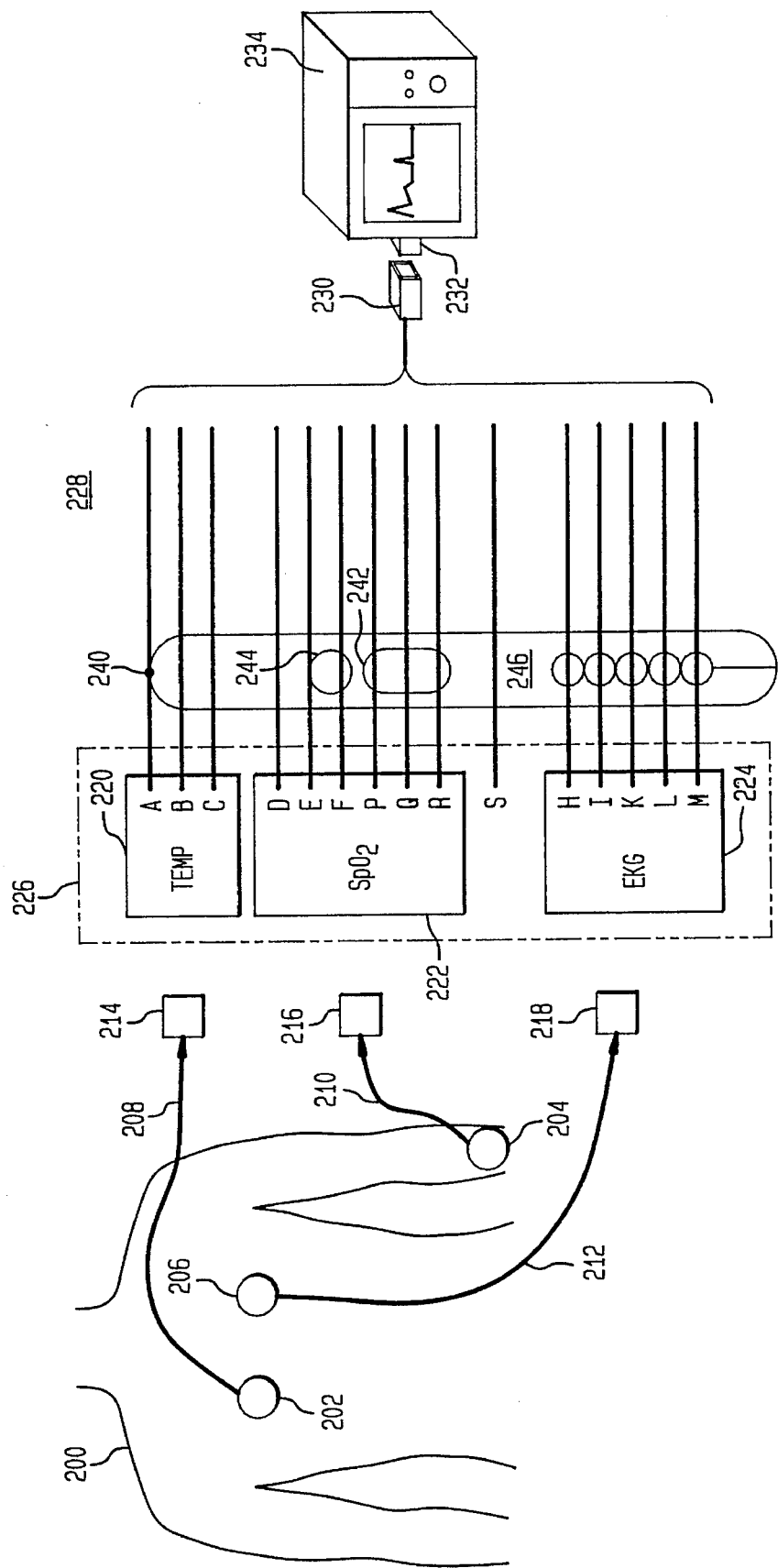
FIG. 2 illustrates a wiring schematic for connecting the conductors from a plurality of patient sensors to a single monitor, in accordance with the principles of the invention.

FIG. 2 illustrates a patient monitoring system which includes a multi-parameter cable constructed in accordance with the principles of the present invention. A patient 200 is symbolically illustrated as including a plurality of sensors mounted thereon for monitoring his vital signs, such as a temperature sensor 202, a non-invasive pulse oximetry sensor 204 and an EKG sensor 206. Respective ones of patient connection leads 208, 210 and 212 have one end connected to sensors 202–206, and their other end connected to a respective one of plugs 214, 216 and 218. The plugs make a mating connection with a respective one of receptacles 220, 222 and 224 of a junction box 226, referred to herein as a pod because it is preferably shaped as a streamline housing and therefore able to be conveniently placed near the patient, such as under his pillow or some other place near or on the patient bed. Pod 226 has a common output cable 228 constructed in accordance with the principles of the present invention, which makes electrical connection at pod 226 with the patient connected cables 208–212, and at its other end includes a plug 230 adapted to mate with a respective socket 232 in a patient monitor 234. The sensors 202–206, patient leads 208–212 and monitor 234 are all conventional patient monitoring apparatuses well known to those of ordinary skill in the art, which provide for the collection, analysis, display and recording of various physiological signs of the patient, and therefore further description of these components is not necessary and therefore omitted.

In a preferred embodiment, the plugs 214, 216, 218 and 230, as well as receptacles 220, 222, 224 and 232, should all provide electromagnetic interference (EMI) shielding for their respective conductors. U.S. Patent Application XXX, XXX entitled FULLY INSULATED, FULLY SHIELDED ELECTRICAL CONNECTOR ARRANGEMENT, filed simultaneously herewith and assigned to the same assignees as the present invention, disclose such a connector shielding technique suitable for use with plugs/receptacles 214/220, 216/222 and 230/232, and is incorporated herein by reference. Briefly, as described therein, the plug and receptacle portion of each connector should be designed so as to completely preserve the EMI shielding provided by the patient leads without compromising the safety of the patient. Additionally, the individual signal carrying conductors extending into pod 226 from plugs 214, 216 and 218 are handled or processed inside the pod for providing RF filtering and signal conditioning before the signals are brought into close proximity with each other in the multi-parameter cable 228. For example, each signal conductor associated with the EKG sensor 206 would preferably be coupled inside pod 226 to a tee-shaped signal processing circuit comprising a series low-pass filter followed by a limiting resistor, a spark gap coupled from the resistor to a common return, and finally a further low-pass filter coupled from the junction of the limiting resistor and spark gap to cable 228. The low-pass filters can each comprise a lossy inductive bead which individually surrounds each insulated EKG signal conductor for limiting the introduction into the monitoring system of, for example, interference signals in the 900 Mhz range from portable radio telephones, as well as electrosurgical signals. The spark gap and limiting resistor are included for attenuating any defibrillator signals which would be picked up by the EKG electrodes in the event that the patient is defibrillated. Inclusion of these filtering techniques within pod 226 is preferable in order to prevent these interference signals from introducing disturbance onto the other conductors within cable 228.

As shown in FIG. 2, multi-parameter cable 228 provides three conductors for monitoring temperature (labelled A, B and C), six conductors for operating the pulse oximetry sensing apparatus (labelled P and Q for carrying the pulse current signals for driving the red and infrared LEDs of the pulse oximetry sensor, labelled R and D for operating the calibration resistor of the sensor and labelled E and F which are connected to the SPO₂ optical receiver and are arranged in a coaxial cable arrangement) and five EKG conductors (labelled H, I, K, L and M) for carrying the EKG signals picked-up by the EKG sensors. Each of these signal conductors has to meet special requirements in order to properly carry its respectively assigned signal. More specifically, conductors A, B, C and R must have a large conductive center to ensure low resistance. Conductors P and Q must also have a large conductive center since they carry relatively high currents. The $SPO_2$ receive conductor, F, carries a very low-level signal, and therefore should provide a high-level of noise shielding, yet also be of low capacitance. Furthermore, each of the EKG conductors must be individually shielded for the reasons previously noted and the shielding must be accomplished in a manner such that flexing of the conductor shield does not create its own electrical noise. An extra conductor S is included in cable 228 for an as yet undecided purpose.

Figure 1A:
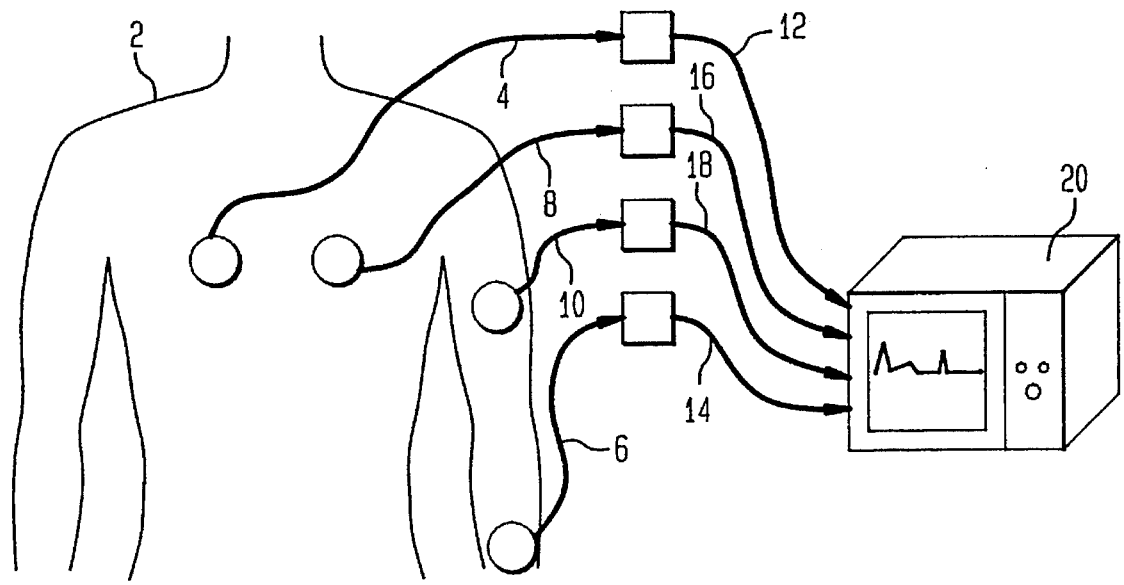
FIGS. 1a and 1b illustrate prior art cable arrangements for a patient monitoring system.
Figure 1B:
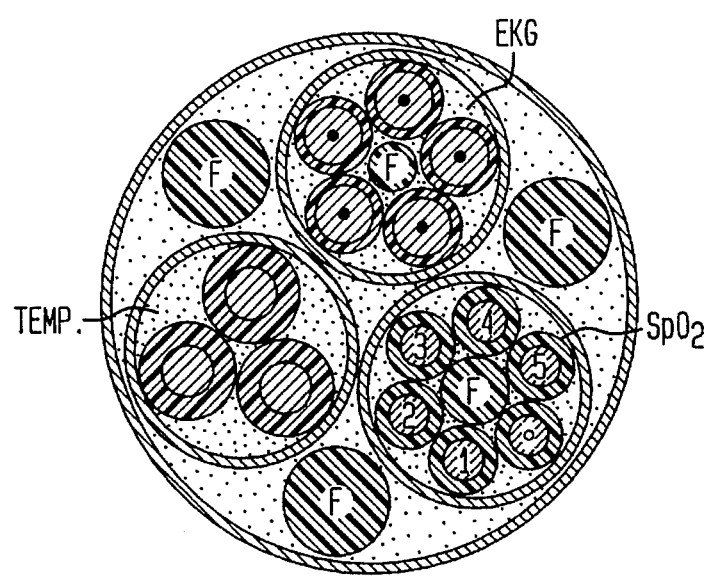

As schematically illustrated in FIG. 2, the shielding requirements for cable 228 are met by an outer or bundle shield 240 which surrounds all of the patient monitoring signal conductors included in cable 228, which is connected at one end to the shield in pod 226 and at its other end to the shield at connector 230, and additional shielding 242, 244 and 246 for other ones of the patient monitoring signal conductors. Shielding 242 is required for the $SPO_2$ signal conductors P and Q which carry pulse signals for driving the light emitting diodes of the conventional pulse oximetry sensor arrangement. Shield 244 is required to protect the $SPO_2$ receive signal conductor and individual shields 246 are required for each of the EKG conductors H, I, K, L and M. Merely bundling the individually shielded conductors, as shown in the FIG. 1a illustration of the prior art, results in a thick, inflexible and heavy cable.

Figure 3:
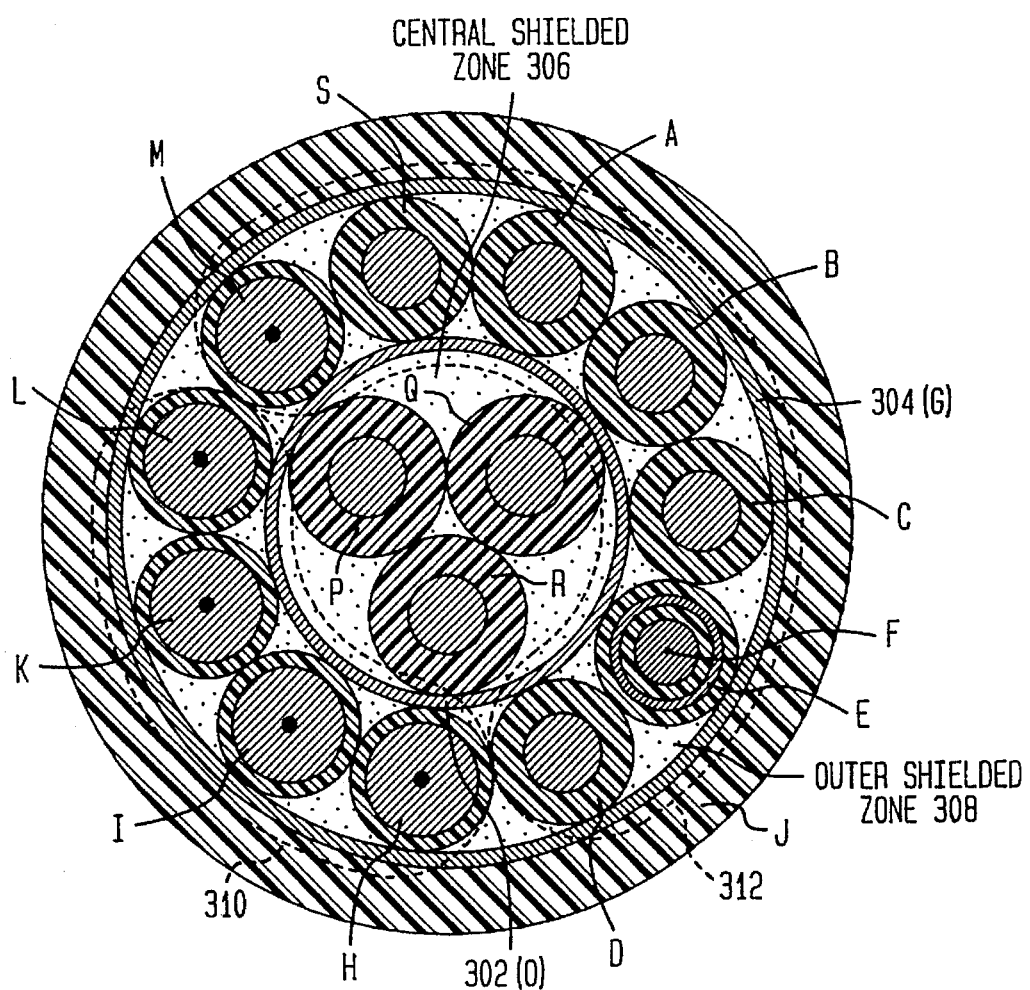
FIG. 3 illustrates a cross-section view of the cable of FIG. 2.

In accordance with the principles of the present invention, all of the forenoted signal handling and shielding requirements for cable 228 are provided by a cable constructed as shown in the cross-section illustrated in FIG. 3. Starting from the inside of the cable, a central or inner zone of the cable is formed by an inner tubular sheath 302, which in the preferred embodiment comprises a copper tinned spiral shield but which, in accordance with a broadest concept of the invention, does not have to be electrically conductive and could merely comprise a plastic sheath. The inner zone defined by sheath 302 provides an ideal space to contain either signal conductors which need the most shielding between them and other conductors relating to the first type of physiological parameter, or signal conductors which should be twisted with respect to each other so that the lay of these conductors is different than the lay of other conductors in the cable in order to cancel the effect of their electromagnetic fields upon the signals carried by the other signal conductors. In the preferred embodiment, although the receive conductor for the pulse oximetry sensor is the most susceptible to noise contamination, it has a relatively small diameter and is therefore a less appropriate choice than bulky twisted conductors, for being located in the center of the multi-parameter cable. Thus, in the preferred embodiment, the central zone is used for carrying conductors P and Q of the pulse oximetry system, which conduct the forenoted relatively high level pulse current LED drive signals and therefore are required to have a large diameter center conductor and to be twisted along the length of the cable so as to have a different lay (twist rate) than other conductors in cable 228, in order to prevent their magnetic fields from differentially affecting the signals carried by the other signal conductors. An additional large diameter conductor, in this case R, which carries the $SPO_2$ return signal for the calibration resistor of the pulse oximeter sensor, is also included in the central zone and twisted with conductors P and Q in order to more effectively utilize the space defined by shield 302. Please note the term twisted is intended to include braiding and other forms of intertwining.

An outer electrically conductive shield 304 is symmetrically disposed and spaced a given distance out from shield 302, thereby defining a space between shields 302 and 304 wherein other ones of the signal carrying conductors can be located. In accordance with one aspect of the invention, these two conductive shields provide a novel and advantageous arrangement for providing electrical isolation between the various groups of signal carrying conductors bundled into the cable. More specifically, inner shield 302 clearly provides an electrically isolated central zone 306 which includes $SPO_2$ conductors P, Q and R arranged in a twisted manner therein. Similarly, spaced outer shield 304 creates an electrically isolated outer zone 308 which is between shields 302 and 304 and contains conductors D, E, and F which are the remaining conductors of the $SPO_2$ sensing arrangement, conductors H, I, K, L and M which conduct the picked-up EKG signals (a second type of physiological parameter) and conductors A, B and C for monitoring temperature (a third type of physiological parameter). In the preferred embodiment, the lay (twist rate) of the conductors in the central zone is twice that of the conductors in the outer zone. Furthermore, not only are the inner and outer zones electrically shielded from each other, but outer shield 304 also provides shielding from interference signals originating from outside cable 228.

In accordance with a further aspect of the invention, the EKG conductors each include an outer electrical conductive shield which is in electrical contact with at least one, and preferably both, of shields 302 and 304. When the conductive outer shields of the EKG electrodes are all adjacent and in physical contact with each other and with one or both of the inner and outer shields 302 and 304, an additional shielded zone 310 is formed, as illustrated by the dashed lines in FIG. 3. Furthermore, through a process of elimination, it is clear that the remainder of the curved space between the inner and outer shields 302 and 304 forms an additional separate electrically shielded zone 312 (illustrated by dashed lines) which comprises that portion of the space between shields 302 and 304 which is not within zone 310. Electrically shielded zone 312 includes conductors A-F and S each of which (except F) has no individual shield, and relies on zone 312 for its shielding requirements.

In accordance with an even further aspect of the invention, the space between shields 302 and 304 is substantially equal to the outside diameter of the shielded EKG conductors. This improves the packing density and shape of cable 228 (and as well as simplifying its construction costs) and efficiently provides for insulated conductors for a third-parameter (temperature) to be included in zone 312 when the insulated conductors of the third parameter are made so as to have substantially the same outside diameter as those of the second parameter (the EKG insulated conductors).

In accordance with a still further aspect of the invention, the symmetric nature of cable 228 is able to be exploited to cost-efficiently provide the necessary resistance to flexing failure for the various metallic conductors of the cable, by using low cost copper conductors in the inner zone and inner shield 302 and only using the more expensive copper alloy conductors in the outer zone and for the outer shield.

The construction and dimension of the individual conductors, shields and cable jacket is indicated in the following table.

| | | |
|---|---|---|
| SPO$_2$ (SEND) | P,Q,R | TINNED COPPER STRANDS INSULATED JACKET, OD 1.15 mm |
| SPO$_2$ (SEND) | D | SILVERPLATED COPPER ALLOY STRANDS |
| TEMP | A,B,C | INSULATED JACKET, OD 1.05 mm |
| SPARE | S | |
| SPO$_2$ (RCV) | F | SILVERPLATED COPPER ALLOY STRANDS INSULATED JACKET, OD 0.42 mm CARBON SHEET, OD 0.62 mm |
| | E | COPPER TINNED SPIRAL SHIELD COVERED WITH INSULATING JACKET, FINAL OD 1.05 mm |
| EKG | H,I,K, L,M | SILVERPLATED COPPER ALLOY STRANDS INSULATION JACKET WITH CARBON SHEET FINAL OD 1.05 mm |
| INNER SHIELD | O | COPPER TINNED SPIRAL SHIELD |
| BUNDLE SHIELD | G | BRAID OF TINSEL WIRES SILVERPLATED |
| JACKET | J | INSULATING JACKET OD 7.2 mm |

It is noted that the individual shields provided for the EKG conductors comprises a carbon-loaded plastic sheet in order to provide an electrically conductive shield which does not create electrostatic noise as a result of flexing. However, these individual EKG shields are not as electrically conductive as stranded copper shields and therefore merely connecting the individual EKG shields to appropriate conductors at the input end and output end of cable 228 would be ineffective, due to the relatively high resistance of the conductive plastic sheet and the length of cable 228. Thus, in accordance with an aspect of the present invention, one or both of shields 302 and 304 is in electrical contact with the full length of the individual EKG shields as they travel through cable 228, thereby reducing the distance between the EKG shields and a reference plane from being the length of the cable to only the diameter of each individual EKG conductor.

The table below cross references the labelled conductors of FIG. 3 with the type of patient monitoring signal carried thereby. Note that the SPO$_2$ receive signal actually comprises a coaxial cable wherein the central portion F conducts a low-level signal current and the SPO$_2$ return signal (labelled E) is carried on an insulated shield which surrounds conductor F.

| | |
|---|---|
| P | PULSE SIGNAL FOR SPO$_2$ RED LED |
| Q | PULSE SIGNAL FOR SPO$_2$ IR LED |
| R | CALIBRATION SIGNAL SPO$_2$ RESISTOR LEAD RETURN |
| D | CALIBRATION SIGNAL SPO$_2$ RESISTOR LEAD |
| A | TEMPERATURE - COMMON |
| B | TEMPERATURE - TA |
| C | TEMPERATURE - TB |
| E | RETURN FOR SPO$_2$ RECEIVE |
| F | SPO$_2$ RECEIVE |
| H | EKG ELECTRODE SIGNAL - RL |
| I | EKG ELECTRODE SIGNAL - RA |
| K | EKG ELECTRODE SIGNAL - LA |
| L | EKG ELECTRODE SIGNAL - LL |
| M | EKG ELECTRODE SIGNAL - V |

Thus, what has been shown and described is a novel construction for an economical, flexible, light-weight, multi-parameter cable which fulfills all the objects and advantages sought therefore. Many changes, modifications, variations and other uses and applications of the subject invention will, however, become apparent to those skilled in the art after considering this specification and its accompanying drawings, which disclose preferred embodiments thereof. For example, although inner shield 302 is conductive, shield 302 could comprise merely a non-conductive tubular sheath and conductors P, Q and R could be individually shielded. Alternatively, the remaining conductors could be individually shielded, like the EKG conductors. Additionally, inner shield 302 could be formed by the air hose of a non-invasive blood pressure apparatus. The outside of the air hose could be made conductive in order to facilitate the shielding effect provided by the individual EKG shields. Furthermore, it should be clear that additional "outer" zones could be provided symmetrically spaced about zone 308, each additional outer zone having its own "lay" of signal conductors. Furthermore, one or more "drain" wires (a bare conductor in physical contact with the metallic shield) can be included, as known in the art. It should also be understood that the term signal conductor is intended to include conductors for signals other than electric ones, e.g., fibers for optical signals or even hoses for air-pressure signals as noted above. All such changes, modifications, variations and other uses and applications which do not depart from the spirit and scope of the invention are deemed to be covered by this patent, which is limited only by the claims which follow as interpreted in light of the foregoing description.

We claim:

1. A flexible multi-parameter conductor cable having coaxially symmetric elongated zones for signal carrying conductor placement therein, comprising:

an electrically conductive inner shield defining an electrically shielded inner longitudinal zone symmetrically disposed along and defining a center of said cable for containing at least one of a first type of signal carrying conductor; and an electrically conductive outer shield spaced a given distance symmetrically around said inner shield so as to define an electrically shielded outer longitudinal zone symmetrically disposed about said inner longitudinal zone for containing a plurality of at least a second type of signal carrying insulated conductor arranged in a single layer adjacent one another as a group in said outer longitudinal zone, said second type of conductor having an electrically conductive outer jacket in electrical contact with said outer shield.

2. The cable of claim 1, wherein said first type of signal carrying conductor comprises a plurality of insulated conductors longitudinally arranged in a twisted manner with respect to each other.

3. The cable of claim 1, wherein the outer jackets of said conductors of said second type are positioned so as to also be in electrical contact with said inner shield, so as to define an additional electrically shielded outer longitudinal zone comprising that portion of said outer longitudinal zone which contains said group of adjacently positioned second type of conductors.

4. The cable of claim 3, further including a third type of signal carrying insulated conductor located in said outer longitudinal zone, which third type of signal carrying conductor comprises the following components, symmetrically arranged in the named order from a center of said third type of conductor: a center electrical conductor surrounded by an electrically conductive shield layer spaced a given distance symmetrically around said center electrical conductor, and including a further insulation surrounding the conductive shield layer, with said second and third type of signal carrying conductors all having an outside diameter which is substantially the same.

5. The cable of claim 3, further including a single layer of a plurality of insulated conductors of a third type coupled to insulated conductors from a third type of sensor, said third type of insulated conductors being arranged adjacent one another between said inner and outer shields so as to be positioned in a group adjacent the group of said second type of conductors, with said second and third type of insulated conductors all having an outer diameter which is substantially the same.

6. The cable of claim 1, wherein said first type of signal carrying conductor comprises an air-tight hose for conducting an air pressure signal therein as an air pressure.

7. The cable of claim 6, wherein said air-tight hose includes an outer surface which is electrically conductive so as to define said inner shield.

8. The cable of claim 6, further including a third type of signal carrying insulated conductor located in said outer longitudinal zone, which third type of signal carrying conductor comprises the following components, symmetrically arranged in the named order from a center of said third type of conductor: a center electrical conductor surrounded by an electrically conductive shield layer spaced a given distance symmetrically around said center electrical conductor, and including a further layer of electrical insulation surrounding the spaced electrically conductive shield layer, with said second and third type of insulated conductors all having substantially the same outside diameter.

9. A cable for use to connect insulated conductors from a plurality of different types of sensors to a monitoring device, wherein insulated conductors from a first type of said sensors are required to have signal handling characteristics which are different from insulated conductors from a second type of said sensors, said cable comprising:

a central portion including a plurality of insulated conductors of a first type adapted to be coupled to the insulated conductors from the first type of sensor, and longitudinally arranged so as to define a length of cable;

an inner tubular sheath which closely surrounds the central portion and extends along the length of the cable; and an electrically conductive outer tubular sheath symmetrically disposed a given distance from said inner tubular sheath and extending along the length of the cable, with insulated conductors of a second type which have a low noise conductive outer sheath arranged adjacent one another in a single layer in a space between said inner and outer tubular sheaths with their outer jackets in electrical contact with said outer sheath and the insulated conductors of the second type adapted to be coupled to the insulated conductors from the second type of sensor.

10. The cable of claim 9, wherein the conductors of the first type are arranged in a twisted manner so as to have a given twist rate per unit length of said cable, and the conductors of said second type are arranged in a twisted manner so as to have a twist rate per unit length of said cable which is different than said given twist rate.

11. The cable of claim 9, wherein the low noise conductive outer sheath comprises a dielectric material having an outer layer treated so as to promote electrical conductivity.

12. The cable according to claim 11, wherein said outer jacket comprises a carbon-loaded plastic sheet.

13. The cable as defined in claim 12, wherein all of said second type of insulated conductors have an outside diameter which are all the same, and said given distance between said sheaths is substantially equal said outside diameter so as to cause the outer jacket of all said second type of insulated conductors to be in physical contact with both of said inner and outer sheaths.

14. The cable as defined in claim 9, wherein said inner sheath comprises an electrically conductive outer portion, and said given distance between said sheaths is substantially equal to an amount needed to allow the outer jacket of said second type of insulated conductor to be in physical contact with both of said inner and outer sheaths.

15. The cable of claim 9, further including a single layer of a plurality of insulated conductors of a third type adapted to be coupled to insulated conductors from a third type of sensor, said third type of insulated conductors being arranged in a group adjacent one another between said inner and outer sheaths.

* * * * *